United States Patent
Musa et al.

(10) Patent No.: US 9,688,631 B2
(45) Date of Patent: Jun. 27, 2017

(54) THERMOSETTING RING-OPENING METATHESIS POLYMERIZATION MATERIALS WITH THERMALLY DEGRADABLE LINKAGES

(75) Inventors: Osama M. Musa, Kinnelon Bedminster, NJ (US); Ezat Khosravi, Durham (GB)

(73) Assignee: ISP Investments LLC, Wilmington, DE (US)

( * ) Notice: Subject to any disclaimer, the term of this patent is extended or adjusted under 35 U.S.C. 154(b) by 296 days.

(21) Appl. No.: 13/203,759

(22) PCT Filed: Mar. 2, 2010

(86) PCT No.: PCT/US2010/025869
§ 371 (c)(1),
(2), (4) Date: Oct. 17, 2011

(87) PCT Pub. No.: WO2010/101882
PCT Pub. Date: Sep. 10, 2010

(65) Prior Publication Data
US 2012/0041137 A1    Feb. 16, 2012

Related U.S. Application Data

(60) Provisional application No. 61/156,738, filed on Mar. 2, 2009.

(51) Int. Cl.
| | | |
|---|---|---|
| C07D 209/94 | (2006.01) | |
| C08F 36/20 | (2006.01) | |
| C08F 26/06 | (2006.01) | |
| C08F 126/06 | (2006.01) | |
| C07D 267/00 | (2006.01) | |
| C08F 34/04 | (2006.01) | |
| C08F 226/06 | (2006.01) | |

(52) U.S. Cl.
CPC ......... *C07D 209/94* (2013.01); *C07D 267/00* (2013.01); *C08F 26/06* (2013.01); *C08F 34/04* (2013.01); *C08F 36/20* (2013.01); *C08F 126/06* (2013.01); *C08F 226/06* (2013.01)

(58) Field of Classification Search
CPC ..... C07D 267/00; C07D 209/94; C08F 34/04; C08F 26/06; C08F 36/20; C08F 126/06; C08F 226/06
USPC ................................................ 526/262, 259
See application file for complete search history.

(56) References Cited

U.S. PATENT DOCUMENTS

| | | | |
|---|---|---|---|
| 3,959,234 A | | 5/1976 | Kurosawa et al. |
| 4,022,954 A | | 5/1977 | Kurosawa et al. |
| 4,837,295 A | * | 6/1989 | Drain et al. .................. 528/111 |
| 5,672,662 A | * | 9/1997 | Harris et al. .................. 525/408 |
| 6,677,418 B1 | * | 1/2004 | Feast et al. .................... 526/281 |
| 7,084,222 B2 | | 8/2006 | Sakamoto et al. |

OTHER PUBLICATIONS

Lee, Neug-Ju et al. "Synthesis and biological activity of medium range molecular weight polymers containing exp-3,6-epoxy-1,2,3,6-tetrahydrophtalimido-caproic acid", 2001, Polymer International, 50, 1010-1015.*
Zhang, Xinnan et al. "Thermallly Degradable Maleimides for Reworkable Adhesives" 2009, Journal of Polymer Science: Part A: Polymer Chemistry, vol. 47, 1073-1084.*

* cited by examiner

*Primary Examiner* — Ling Choi
*Assistant Examiner* — David L Miller
(74) *Attorney, Agent, or Firm* — William J. Davis

(57) ABSTRACT

The present invention provides a new class of thermosetting ring-opening metathesis polymerization materials based on norbornene and oxanorbornene dicarboximide moieties containing at least one acetal ester group linkage. The acetal ester group is degradable when subjected to heat or acidic aqueous hydrolysis. The polymerization materials can be used in reworkable thermosetting compositions. R1-Rs, X, and n are defined herein.

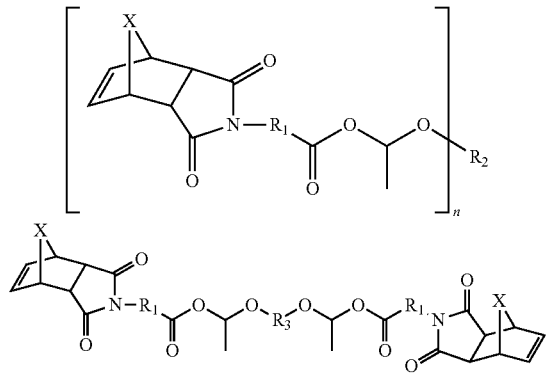

8 Claims, No Drawings

THERMOSETTING RING-OPENING METATHESIS POLYMERIZATION MATERIALS WITH THERMALLY DEGRADABLE LINKAGES

BACKGROUND OF THE INVENTION

Field of the Invention

The present invention provides a new class of thermosetting ring-opening metathesis polymerization materials based on norbornene and oxanorbornene dicarboximide moieties containing at least one acetal ester group linkage. The acetal ester group is degradable when subjected to heat or acidic aqueous hydrolysis. The polymerization materials can be used in reworkable thermosetting compositions.

Description of Related Art

Thermosetting polymers are an important class of materials and have been used in a wide range of applications because of their excellent thermal and mechanical properties, particularly as coatings, adhesives, and encapsulants. However, traditional thermosetting materials generally display good durability, poor tractability, and poor biodegradability. These characteristics limit their use particularly in those applications for which degradable or reworkable polymers are advantageous in many industries, such as in electronics, recycling, and biodegradation. For example, the reworkability of an adhesive employed in semiconductor chips is desirable because it is costly to discard a multi-chip package with a single failed chip. The use of an adhesive that will decompose to allow chip repair or replacement would be very desirable for semiconductor manufacturers. Thus, there is a need for adhesives, coatings, and encapsulants that can be reworked in many applications.

Ring-opening metathesis polymerization (ROMP), initiated by well-defined ruthenium initiators, have been shown to display excellent functional group tolerance and allows the synthesis of well-defined polymers with controlled architectures, molecular weights, polydispersities, and terminal functionalities. ROMP processing techniques have also been developed for the synthesis of thermosetting materials with well-defined crosslinked networks from mixtures of monofunctional and difunctional monomers using ruthenium initiators for applications in Resin Transfer Moulding (RTM) and Reaction Injection Moulding (RIM). By this ROMP processing technique, an excellent level of control over crosslink density and hence over material properties has been developed. The crosslinked materials produced show high values of yield strength and toughness, which are either comparable or better than the engineering polymer materials, such as polycarbonates which are not easy to synthesize and process. The ROMP thermosetting materials are thermally stable >400° C. and can be used for applications where high temperature stability is required.

A number of different types of degradable linkages have previously been studied. Polymers containing acetal or ketal groups along the main chain have been reported which are shown to degrade into low molecular weight compounds by acid-catalysed hydrolysis. Recently, thermally degradable carbamate and carbonate linkages have been introduced into epoxy-based adhesive formulations to facilitate the reworking process. Most of the degradable thermosetting materials that have been reported in the literature are based on traditional epoxy resin systems and maleimide resin systems containing acetal ester groups.

SUMMARY OF THE INVENTION

The present invention provides compounds comprising norbornene and oxanorbornene dicarboximide functionality and at least one acetal ester linkage. The acetal ester group is degradable when subjected to heat or acidic aqueous hydrolysis. Examples of the novel compounds include:

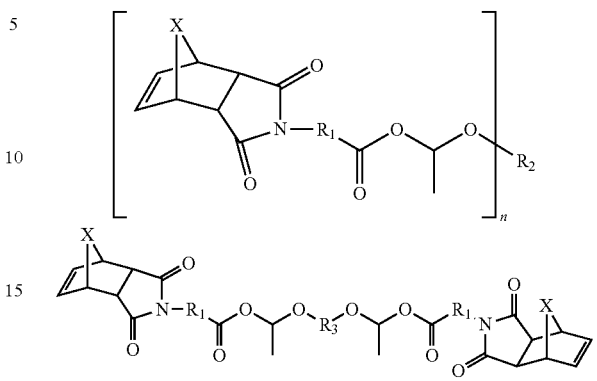

wherein X is independently $CH_2$ or O; $R_1$, $R_2$, and $R_3$ are independently selected from the group consisting of unsubstituted or substituted alkyl, cycloalkyl, alkenyl, and aryl groups, wherein any of the before mentioned groups may be present with or without heteroatoms; wherein each $R_1$ group is further independently selected from any of the before mentioned groups; and n is from 1 to about 500.

The novel compounds are synthesized by the reaction of a norbornene or oxanorbornene dicarboxylic anhydride with a terminal aminocarboxylic acid. The resulting norbornene or oxanorbornene dicarboximide is then reacted with a vinyl ether to form a norbornene or oxanorbornene dicarboximide moiety containing at least one acetal ester group linkage.

In another embodiment, this invention is a reworkable material composition comprising a thermosetting compound containing acetal ester group linkages. The crosslinked material is the product of a ring-opening metathesis polymerization of norbornene or oxanorbornene dicarboximide moieties containing at least one acetal ester linkage. The thermosetting compound is degradable when subjected to heat or acidic aqueous hydrolysis and provides the reworkable aspect of the invention.

The present invention further provides compositions comprising the above material containing norbornene or oxanorbornene dicarboxylic functionality and at least one acetal ester linkage and also compositions comprising the crosslinked material which is the product of a ring-opening metathesis polymerization of norbornene or oxanorbornene dicarboximide moieties containing at least one acetal ester linkage. The composition may be an adhesive, coating, encapsulation, personal care, oilfield, membrane, agricultural, or cleaning composition.

DETAILED DESCRIPTION OF THE INVENTION

The present invention provides thermosetting ROMP materials degradable by introducing acetal ester linkages into crosslinkable structures. These materials have three attractive advantages. First, the method by which these well-defined crosslinked ROMP materials are produced is versatile and allows the introduction of "sticky" functional groups into the monomer systems to promote adhesion to a wide range of substrates. Therefore, thermosetting ROMP materials containing thermally degradable linkages developed here have potential use as adhesives in a variety of applications, particularly in the electronics industry. Second, the decomposition of the thermally degradable crosslinks will lead to a decrease in crosslinking density and modulus. The complete breakdown of all linkages produces linear thermoplastic materials providing the main-chains remain intact. This will promote the recycling of thermosetting materials which is presently difficult to achieve. Third, the incorporation of biodegradable linkages into these thermosetting materials will result in materials which are tough and yet degradable leading to the breakdown of the bulk material.

As used herein, the following terms have the meanings set out below.

The term "compound comprising a norbornene or an oxanorbornene dicarboximide functionality" employs the term "comprising" which is an "open ended term" that means that the claim encompasses all of the elements listed as well as additional, unnamed elements, such as a compound containing both a norbornene and an oxanorbornene functionality.

The term "heteroatom" refers to atoms such as oxygen, nitrogen, sulfur, and phosphorous.

The term "norbornene" refers to compounds having the general structure:

The term "monomer" refers to the repeat units comprising a polymer. A monomer is a small molecule that chemically bonds to other monomers to form a polymer.

The term "oxanorbornene" refers to compounds having the general structure:

The term "polymer" refers to a large molecule (macromolecule) composed of repeating structural units (monomers) connected by covalent chemical bonds.

The term "resin" may be used interchangeably with the term polymerization materials that can be used in the reworkable thermosetting compositions.

The term "ROMP" refers to "ring-opening metathesis polymerization" which is an adaptation of olefin metathesis, where cyclic olefins are polymerized using transition metal complexes as initiators. Cyclic olefins are usually reacted with linear olefins to generate acyclic dienes. The reaction makes use of strained ring systems, such as norbornene and oxanorbornenes, and their derivatives to produce an array of stereoregular and monodisperse polymers and copolymers.

The present invention provides compounds comprising norbornene and oxanorbornene dicarboximide functionality and at least one acetal ester linkage. The invention is the first example of thermosetting ROMP materials based on norbornene and oxanorbornene dicarboximide networks containing acetal ester groups as degradable linkages by thermal means or acidic aqueous hydrolysis. The synthesis of monofunctional and difunctional norbornene dicarboximide monomers containing acetal ester linkages is shown below in Scheme 1.

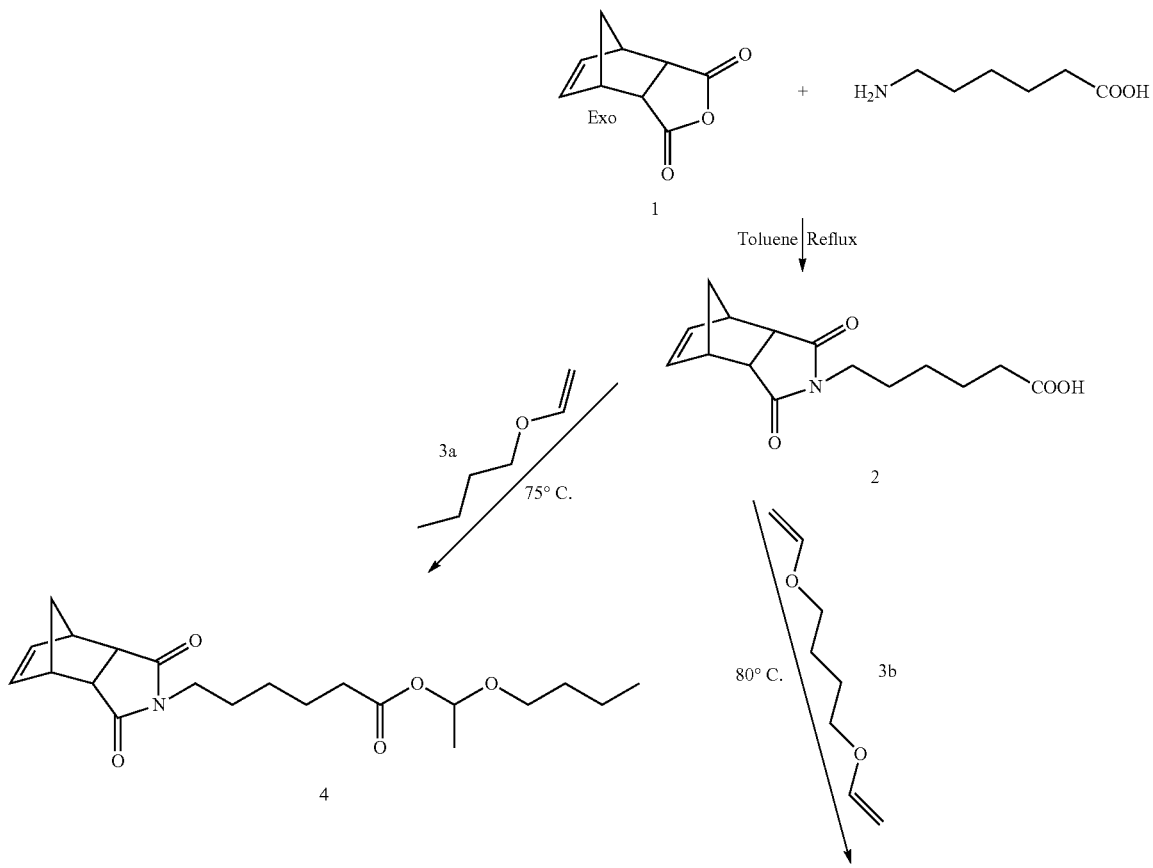

Scheme 1

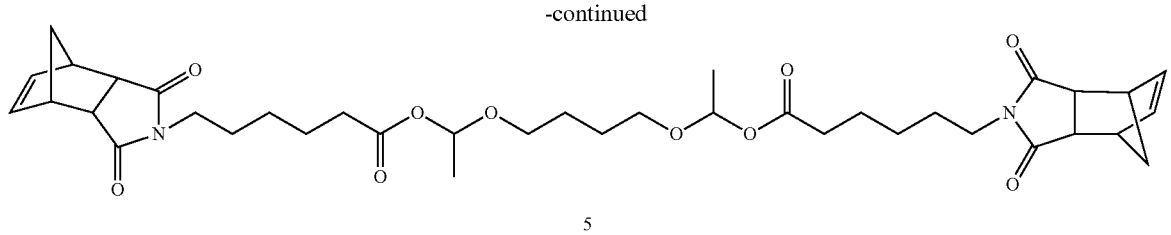

5

The syntheses of monomers was accomplished by the reaction of exo-norbornene dicarboxylic anhydride (1) with a terminal aminocarboxylic acid (6-aminocaproic acid). The resulting exo-norbornene dicarboxyimidocaproic acid (2) was then reacted with butyl vinyl ether (3a) and 1,4-butanediol divinyl ether (3b) to form a norbornene dicarboximide moiety containing one or more acetal ester group linkages, respectively, monofunctional monomer (4) and difunctional monomer (5). Each monomer was characterized by a variety of techniques including nuclear magnetic resonance (NMR), Fourier Transform Infrared Spectroscopy (FT-IR), mass spectroscopy (MS), and elemental analyses. A similar procedure can be carried out to prepare monomers containing oxanorbornene dicarboximide functionality.

Non-limiting examples of norbornene and oxanorbornene imidocarboxylic acids may be represented by the following structure:

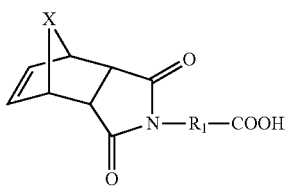

A preferred norbornene imidocarboxylic acid has the following structure:

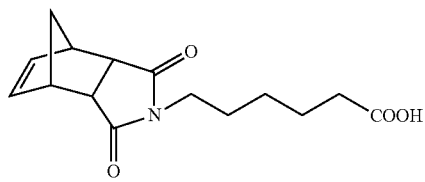 [SMILES: O=C(O)CCCCCN1C(=O)C2C3C=CC(C3)C2C1=O]

Examples of the novel norbornene and oxanorbornene dicarboximides monomers include:

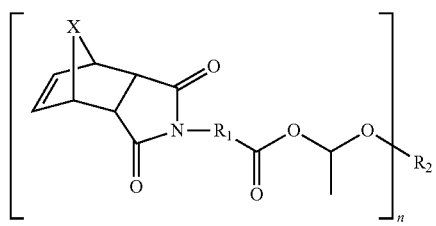

Examples of the novel difunctional norbornene and oxanorbornene dicarboximide monomers include:

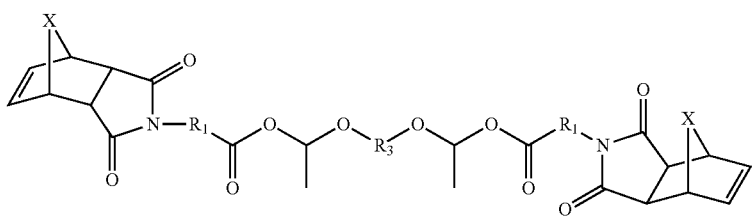

wherein X is independently $CH_2$ or O; and $R_1$ is selected from the group consisting of unsubstituted or substituted alkyl, cycloalkyl, alkenyl, and aryl groups, wherein any of the before mentioned groups may be present with or without heteroatoms.

In the norbornene and oxanorbornene dicarboximide monomers above, X is independently $CH_2$ or O; $R_1$, $R_2$, and $R_3$ are independently selected from the group consisting of unsubstituted or substituted alkyl, cycloalkyl, alkenyl, and aryl groups, wherein each $R_1$ group is further independently selected from any of the before mentioned groups; wherein any of the before mentioned groups may be present with or without heteroatoms; and n is 1 to about 500.

Preferably, X is $CH_2$. Preferably, the alkyl and alkenyl groups may be branched or unbranched (straight-chain). Preferably, the alkyl and alkenyl group is a $C_1$-$C_8$, more preferably a $C_1$-$C_6$, and most preferably a $C_1$-$C_5$ group.

Cycloalkyls (closed rings) include cyclopentane, cyclohexane, cycloheptane, and the like. Aryl groups include benzenes, naphthalenes (2 rings), and anthracenes (3 rings), aromatic heterocyclic compounds, and the like. Heteroatoms include oxygen, nitrogen, sulfur, and phosphorous. Preferably, n is 1 to about 400

A preferred monofunctional norbornene dicarboximide monomer is represented by the following structure:

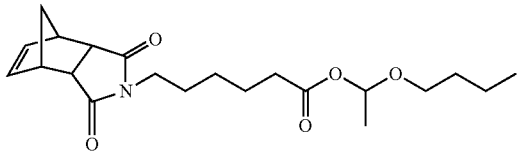 [SMILES: CCCCOC(C)OC(=O)CCCCCN1C(=O)C2C3C=CC(C3)C2C1=O]

A preferred difunctional norbornene dicarboximide monomer is represented by the following structure:

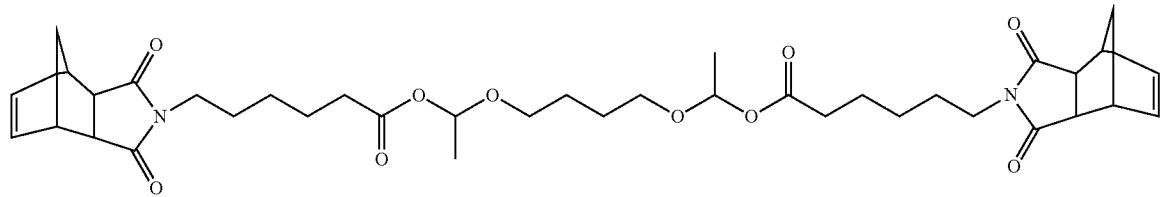 [SMILES: CC(OCCCCOC(C)OC(=O)CCCCCN1C(=O)C2C(C1=O)C1CC13C=CC23)OC(=O)CCCCCN1C(=O)C2C(C1=O)C1CC13C=CC23]

These monomers can then be subsequently polymerized by the ROMP technique using ruthenium generation initiators and other transition metal initiators (Mo, W, and the like), both well defined and not so well defined, to afford a selection of crosslinked thermosetting materials. Illustrative non-limiting examples of ROMP initiators are disclosed in US Patent Application Publication US/2005/0283026 and WIPO 2005/121158, which disclosures are incorporated herein by reference. Hence, the present invention provides materials resulting from ring-opening metathesis polymerization of norbornene and oxanorbornene dicarboximide moieties containing at least one acetal ester group linkage and the resulting material contains acetal ester linkages.

The present invention further provides a composition comprising a material resulting from ring-opening metathesis polymerization of norbornene or oxanorbornene dicarboximide moieties containing at least one acetal ester group linkage and the resulting material contains acetal ester linkages. The composition may be an adhesive, coating, encapsulation, personal care, oilfield, membrane, agricultural, or cleaning composition.

The syntheses of materials 6-9 (see Examples) were carried out via ROMP using $1^{st}$ generation ruthenium initiator in chloroform at ambient temperature. Difunctional monomer 5 was subjected to ROMP to produce crosslinked materials 6a and 6b. Materials 6a and 6b are two batches that were prepared to test the reproducibility of the ROMP process. These materials were insoluble in common organic solvents. The FT-IR spectra of the materials clearly showed the presence of an acetal C—O band at 1135 cm$^{-1}$. The materials are stable to 150° C. and only a few percent weight loss is observed which is due to the moisture contaminant or residual solvents in the materials. However, the materials showed average weight loss of 13%, 20% and 30% at 200° C. 250° C. and 300° C., respectively, Table 1. The materials were also subjected to TGA-MS analysis to determine the fragments resulting from thermal decomposition of the materials by taking sequential mass spectrometric traces at 50° C. intervals.

The fragments obtained from TGA-MS analysis are tabulated below in Table 1. The most abundant fragments detected for the degradation of these materials were between 200° C. and 250° C., possessed m/z ratios of 44, 55, 72 and 101 mass units. Retrieved materials following TGA-MS were subjected to FT-IR analysis, and it was found that the intensity of the acetal C—O band at 1135 cm$^{-1}$ was reduced.

TABLE 1

TGA-MS for materials 6-9

| Temp. | Weight Loss % | | | | | Fragments Observed |
|---|---|---|---|---|---|---|
| ° C. | 6a | 6b | 7 | 8 | 9 | m/z ratio |
| 100 | 1.5 | 1 | 1 | 0.5 | 0.5 | 44 |
| 150 | 5.8 | 3 | 4 | 1 | 1 | 44 |
| 200 | 13 | 13 | 13 | 8 | 9 | 44, 55, 72, 101 |
| 250 | 19 | 21 | 37 | 25 | 21 | 44, 55, 72, 101 |
| 300 | 28 | 31 | 45 | 37 | 26 | 44, 55, 72, 101 |
| 350 | 30 | 34 | 58 | 45 | 31 | 44 |
| 400 | 35 | 38 | 66 | 49 | 34 | 44 |

Materials were prepared from the ROMP of mixtures of difunctional 5 and monofunctional 4 monomers to produce materials with different degrees of crosslinking. Three materials were prepared using molar ratios of difunctional: monofunctional monomer of 75:25; 50:50, and 25:75, labelled 7, 8 and 9, respectively. The materials were insoluble in common organic solvents. The FT-IR spectrum showed the presence of an acetal C—O band at 1135 cm$^{-1}$. The sol-gel analysis of crosslinked materials 6-9 revealed gel contents of 79-89% indicating the high efficiency of the ROMP crosslinking process.

The thermal degradation of the materials 7-9 was studied by TGA from 25° C. to 400° C. at a rate of 10° C. min$^{-1}$. The weight loss was found to be 37%, 25% and 21%, respectively, for materials 7, 8 and 9 at 250° C. This weight loss is consistent with material 7 having the most difunctional content and hence the highest degree of crosslinking and material 9 having the least difunctional and hence the least degree of crosslinking.

Materials 7-9 were also subjected to TGA-MS analysis to determine the fragments resulted from thermal decomposition of the materials by taking sequential mass spectrometric traces at 50° C. intervals. The fragments obtained are also tabulated in Table 1. The TGA-MS analysis also showed fragments possessing m/z ratios of 44, 55, 72 and 101 mass units when the materials were heated between 200° C. and 250° C.

Retrieved materials following TGA-MS were subjected to FT-IR analysis, and it was found that the intensity of acetal C—O band was reduced. The reduction in the intensity of the C—O band again suggests a change in the acetal ester linkages of the material networks which is believed be the result of the decomposition of the acetal ester group.

It is clear from Table 1 that the same fragments are observed in the breakdown of the materials 6a, 6b and materials 7-9 during the TGA-MS analysis of the material networks. These fragments and their proposed structures are shown in Table 2. The thermal decomposition of the acetal ester group is believed to give an acetaldehyde compound which corresponds to the fragment observed with an m/z ratio of 44 mass units. Further cleavage of the acetal ester groups is believed to lead to the formation of butenyl ethyl ether, butenyl alcohol, butadiene with m/z of 101, 72, and 55 units respectively.

TABLE 2

| Fragments m/z ratio | Proposed corresponding structures |
|---|---|
| 44 |  Acetaldehyde |
| 55 | 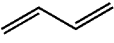 Butadiene |
| 72 | 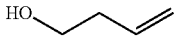 Butenyl alcohol |
| 101 | 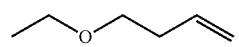 Butenyl ethyl ether |

The compounds of the present invention can be prepared according to the examples set out below. The examples are presented for purposes of demonstrating, but not limiting, the preparation of the compounds and compositions of this invention.

EXAMPLES

In accordance with the present invention, the following examples are provided to illustrate preferred methods for preparing a new class of thermosetting ROMP materials based on norbornene dicarboximide networks containing acetal ester groups as thermally degradable linkages.

Materials and Methods 6-amino caproic acid (>99%), 1,4-butanediol divinyl ether (98%), 4-methoxyphenol (99%), Amberlyst A21 free base, Grubbs' catalyst 1$^{st}$ generation, and butyl vinyl ether (98%) were purchased from Aldrich and used as received. Toluene, chloroform and dichloromethane were acquired from the departmental solvent purification system.

All reactions were carried out under an atmosphere of nitrogen, or in an M-Braun 150B-G glove box. All ROMP conversions were undertaken in a glove box. NMR spectra were either recorded on a Bruker Avance 400 spectrometer at 400.0 MHz ($^1$H) and 100.6 MHz ($^{13}$C); or a Varian Inova 500 spectrometer at 499.8 MHz ($^1$H, COSY, HSQC) and 125.7 MHz ($^{13}$C); all chemical shifts were referenced to the residual proton impurity of the deuterated solvent, CDCl$_3$ unless otherwise stated. Melting points were determined on Electrothermal 1A 9100 apparatus. Infrared spectra were recorded using a Perkin Elmer RX1 FT-IR machine. Elemental Analyses were carried out on an Exeter Analytical E-440 elemental analyzer. Mass Spectral analyses were carried out on a micromass LCT using positive and negative ionization electrospray modes as specified.

Thermogravimetric analysis-mass spectrometry (TGA-MS) measurements were performed using a Perkin Elmer Pyris 1 TGA in conjunction with a Hiden HPR20. For TGA-MS experiments 3.0 to 15.0 mg of the material were heated in an inert atmosphere from 25° C. to 400° C. at a heating rate of 10° C. min$^{-1}$. Mass spectra were taken sequentially at intervals of 50° C.

The gel fraction contents of crosslinked polymers 6-9 were determined by sol-gel extraction in boiling chloroform or dichloromethane, followed by thorough drying in a vacuum oven for one day at 50° C. The gel fraction content (percent) was determined as a ratio of the final weight after extraction and drying, W$_{final}$, divided by the initial weight before extraction, W$_{initial}$.

$$\text{Gel content}(\%) = \frac{W_{final}}{W_{initial}} \times 100$$

All gel contents of the crosslinked materials are quoted in their synthesis sections.

Example 1

Synthesis of Monomers

Exo-Norbornene Dicarboxylic Anhydride (1)

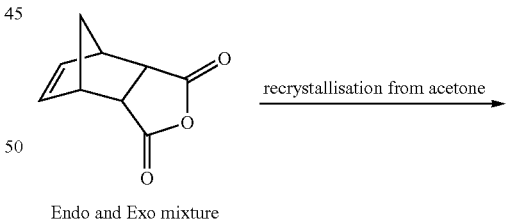

A mixture of exo-/endo-isomers of norbornene dicarboxylic anhydride was prepared according to the literature. The pure exo isomer was obtained by recrystallization of the mixture from acetone.

The mixture of endo/exo isomers, containing 80% exo, (27.33 g) and a stirrer bar were placed in a round bottom flask (250 ml) fitted with a reflux condenser. Acetone (40 ml) was added and the mixture was refluxed until the solid was completely dissolved. The mixture was then left to re-crystallize. The crystals were then filtered and dried in a vacuum oven at room temperature. The final product was obtained as white crystals in a 68% yield (18.01 g, 110 mmol). The structure was confirmed by NMR and FT-IR.

Example 2

N-Caproic Acid-Exo-Norbornene Dicarboximides (2)

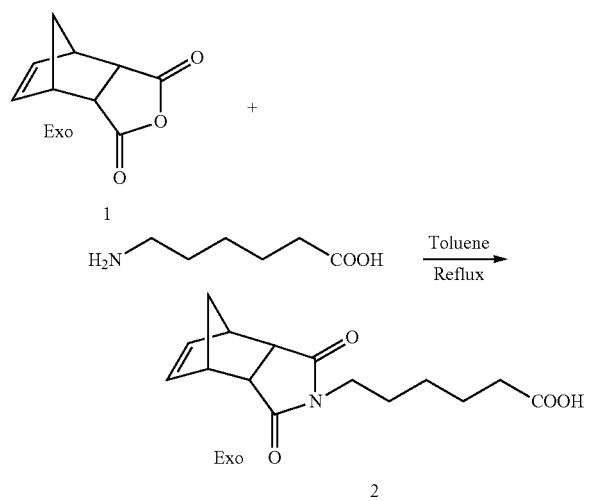

Exo-norbornene dicarboxylic anhydride (1) (2.5 g, 15.2 mmol), 6-aminocaproic acid (2.2 g, 16.8 mmol) and a stirrer bar were placed in a dry two necked round bottom flask (100 ml), fitted with a reflux condenser and kept under nitrogen. Toluene (dry, 10 ml) was added to the flask and the mixture was heated to 115° C. and left for 17 hours. The flask was cooled to room temperature and toluene was removed by rotary evaporation. The crude product was re-crystallized twice from ethyl acetate. The product was dried in a vacuum oven at room temperature. The product 2 was obtained as a white powder in an 83% yield (3.52 g, 12.7 mmol). The structure was confirmed by NMR and MS.

The reaction was scaled up using exo-norbornene dicarboxylic anhydride (15.51 g, 94 mmol), 6-aminocaproic acid (13.63 g, 103 mmol) in toluene (dry, 65 ml) in a two-necked round bottom flask (250 ml), obtaining 25.04 g (90.2 mmol) of compound 2 (95% yield).

Example 3

Monofunctional Monomer (4)

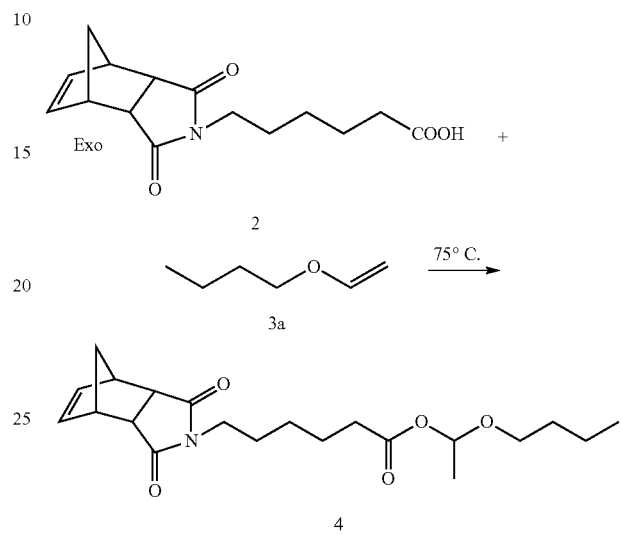

Butyl vinyl ether (3a, 2.00 g, 20 mmol), 4-methoxyphenol (0.016 g, 0.13 mmol) and a stirrer bar were added to a dry two necked round bottom flask (250 ml), fitted with a dry ice reflux condenser and kept under nitrogen. The mixture was heated to 75° C. and compound 2 (3.05 g, 11 mmol) was added in 10 stepwise portions over a period of 2 hours. The mixture was stirred for 12 hours under nitrogen at 75° C. The reaction mixture was allowed to reach the ambient temperature. Amberlyst A21 free base ion exchange resin (4.76 g) and toluene (dry, 20 ml) were then added and the mixture was stirred for a further two hours. The Amberlyst A21 was removed by filtration, and toluene was removed under reduced pressure on a rotary evaporator. The product was then dried under reduced pressure at room temperature. The final product was obtained as a viscous orange-brown liquid in a 50% yield (2.09 g, 5.5 mmol). The structure was confirmed by NMR and FT-IR.

Example 4

Difunctional Monomer (5)

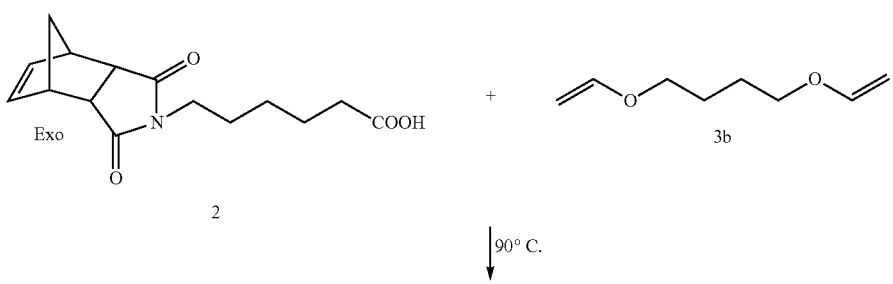

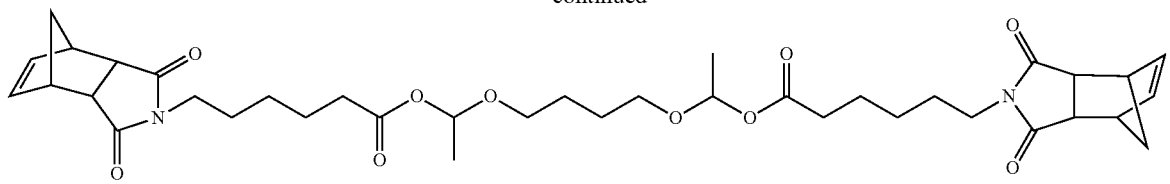

5

1,4 butanediol divinyl ether (3b, 0.71 g, 5 mmol), 4-methoxyphenol (0.016 g, 0.13 mmol) (inhibitor) and a stirrer bar were added to a dry two necked round bottom flask (250 ml), fitted with a reflux condenser and kept under nitrogen. The reaction mixture was heated to 90° C. and compound 2 (3.05 g, 11 mmol) was added in 10 stepwise portions over a period of two hours. The colorless mixture turned orange with the addition of 2. The mixture was left to stir for 21 hours at 90° C. under nitrogen. The reaction mixture was allowed to reach room temperature. Amberlyst A21 free base ion exchange resin (4.76 g) and toluene (dry, 19 ml) was added and the mixture was stirred for a further two hours. The Amberlyst A21 was removed by filtration, and the toluene was removed under reduced pressure on a rotary evaporator. The product was then dried under reduced pressure at room temperature. The final product 5 was obtained as a highly viscous orange-brown liquid in a 50% yield (1.741 g, 2.50 mmol). The structure was confirmed by NMR and FT-IR.

Example 5

Synthesis of Crosslinked Materials

Crosslinked Materials 6a and 6b material was formed soon after the addition of initiator to monomer. The crosslinked product was filtered and dried in a vacuum oven at 50° C. for 18 hours. A known amount of the product was subjected to a sol-gel extraction to remove any soluble fractions. TGA-MS analysis was performed on the dried material. The retrieved material after TGA-MS analysis was found to be insoluble in $CDCl_3$. Monomer: Initiator ratio=55:1; Gel content: 73% ($W_{initial}$, 0.222 g; $W_{final}$, 0.161 g); FT-IR before TGA (neat), $v/cm^{-1}$: 2926 (C—H), 1694 (C=O), 1135 (acetal C—O); FT-IR after TGA (neat), $v/cm^{-1}$: 2929 (C—H), 1690 (C=O), 1146 (acetal C—O).

TGA-MS Data for 6a

| Temperature/° C. | % Weight loss | Fragments observed on MS trace (m/z ratio) |
| --- | --- | --- |
| 100 | 1.5 | 44 |
| 150 | 5.8 | 44 |
| 200 | 13.0 | 44, 55, 72, 101 |
| 250 | 18.7 | 44, 55, 72, 101 |
| 300 | 26.5 | 44 |
| 350 | 29.5 | 44 |
| 400 | 34.1 | 44 |

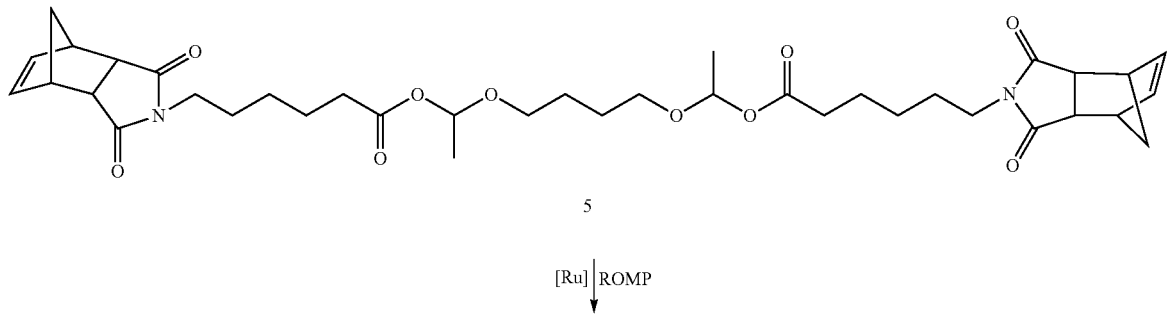

5

[Ru] | ROMP

Crosslinked Polymer (Thermosetting) (6a and 6b)

Monomer 5 (1.636 g, 2.35 mmol) was dissolved in dichloromethane (dry, 4.5 ml) to prepare a stock solution of the monomer because of the viscosity of the monomer. The solution was transferred to a Young's ampule under nitrogen, and then subsequently transferred to the glove box.

Crosslinked Material 6a

Difunctional monomer 5 (1.5 ml of the stock solution) was measured into a material vial equipped with a magnetic stirrer. Ruthenium 1st generation initiator (0.0113 g, 0.0137 mmol) was dissolved in dichloromethane (dry, 1.5 ml) and was added to the vial containing monomer. A crosslinked Crosslinked Material 6b Ruthenium 1st generation catalyst (0.0117 g, 0.0142 mmol) was dissolved in dichloromethane (1.5 ml) containing a stirrer bar. Difunctional monomer 5 (1.5 ml stock solution) was added to the vial containing the initiator. A crosslinked material is formed soon after the addition of initiator to monomer. The crosslinked product was filtered and dried in a vacuum oven at 50° C. for 18 hours. A known amount of the product was subjected to a sol-gel extraction to remove any soluble fractions. TGA-MS analysis was performed on the dried material. The retrieved material after TGA-MS analysis was found to be insoluble in $CDCl_3$. The retrieved material found to be insoluble in CDCl$_3$. (Monomer:Initiator ratio=57:1; Gel Content: 89% (W$_{initial}$, 0.172 g; W$_{final}$, 0.153 g); FT-IR before TGA (neat), v/cm$^{-1}$: 2937 (C—H), 1693 (C=O), 1133 (acetal C—O); FT-IR after TGA (neat), v/cm$^{-1}$: 2937 (C—H), 1683 (C=O), 1146 (acetal C—O).

TGA-MS Data for 6b

| Temperature/° C. | % Weight loss | Fragments observed on MS trace (m/z ratio) |
|---|---|---|
| 100 | 0.6 | 44 |
| 150 | 2.2 | 44 |
| 200 | 14.5 | 44, 55, 72 |
| 250 | 30.1 | 44, 55, 72 |
| 300 | 45.4 | 44 |
| 350 | 49.6 | 44 |
| 400 | 53.2 | 44 |

Example 6

Crosslinked Materials 7, 8, and 9 vial containing a small stirrer bar. The monomer mixture was then added to the initiator and stirred until a crosslinked product was yielded. The crosslinked product was filtered and dried in a vacuum oven at 50° C. for 18 hours. A known amount of the product was subjected to a sol-gel extraction to remove any soluble fractions. TGA-MS analysis was performed on the dried material. The retrieved material after TGA-MS analysis was found to be insoluble in CDCl$_3$.

Crosslinked Material 7 (m=3, n=1)

Monomer:Initiator ratio=57:1; Gel Content: 82% (W$_{initial}$, 0.222 g; W$_{final}$, 0.181 g); FT-IR before TGA (neat), v/cm$^{-1}$: 2929 (C—H), 1692 (C=O), 1135 (acetal C—O); FT-IR after TGA (neat), v/cm$^{-1}$: 2934 (C—H), 1695 (C=O), 1146.5 (acetal C—O).

TGA-MS Data

| Temperature/° C. | % Weight loss | Fragments observed on MS trace (m/z ratio) |
|---|---|---|
| 100 | 0.7 | 44 |
| 150 | 3.7 | 44 |
| 200 | 12.9 | 44, 55, 72, 101 |
| 250 | 36.5 | 44, 55, 72, 101 |
| 300 | 44.9 | 44, 55, 72 |
| 350 | 57.9 | 44 |
| 400 | 65.7 | 44 |

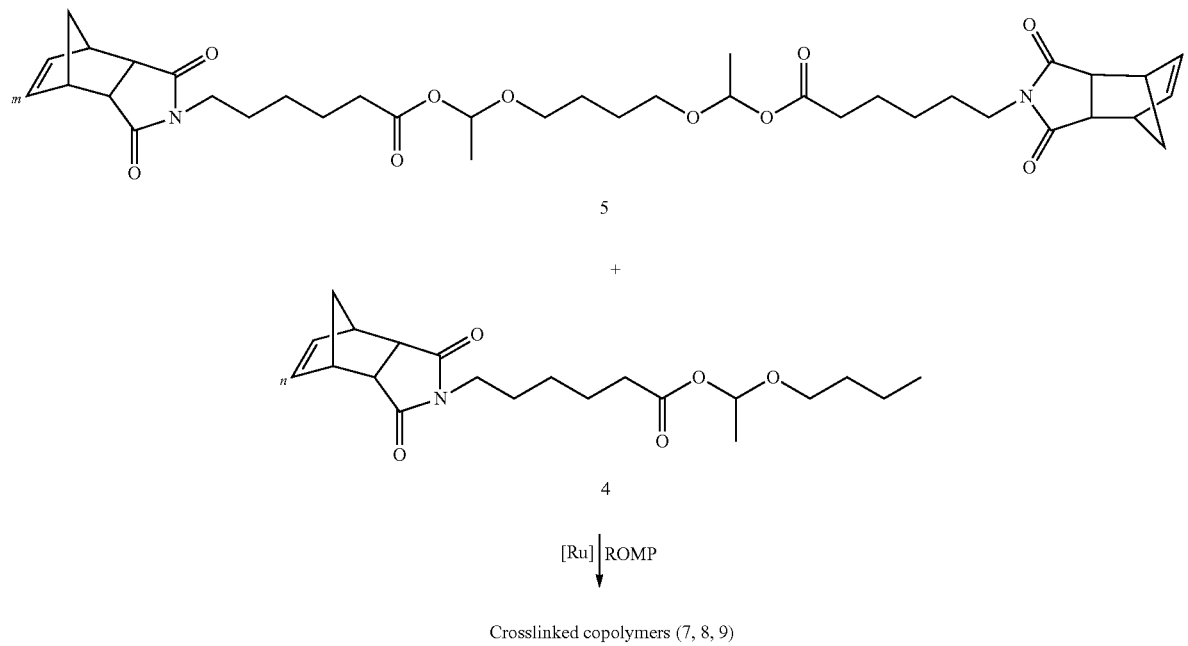

Monomer mixtures were prepared in material vials by the addition of the difunctional monomer 5 and monofunctional monomer 4. The molar ratios of the monomers in the mixture are shown in the table below.

| Material | No. of moles of monomer 5 (m)/mmol | No. of moles of monomer 4 (n)/mmol | Total moles of monomer (m + n)/mmol | Ratios of 5:4 |
|---|---|---|---|---|
| 7 | 0.39 | 0.13 | 0.52 | 75:25 |
| 8 | 0.26 | 0.26 | 0.52 | 50:50 |
| 9 | 0.13 | 0.39 | 0.52 | 25:75 |

To each material vial was added dichloromethane (2.5 ml). Ruthenium 1$^{st}$ generation initiator (0.0079 g, 0.0096 mmol) dissolved in dichloromethane (1.5 ml) in a material Crosslinked Material 8 (m=1, n=1)

Monomer:Initiator ratio=57:1; Gel Content: 79% (W$_{initial}$, 0.202 g; W$_{final}$, 0.162 g); FT-IR before TGA (neat), v/cm$^{-1}$: 2919 (C—H), 1692 (C=O), 1133 (acetal C—O); FT-IR after TGA (neat), v/cm$^{-1}$: 2924 (C—H), 1694 (C=O), 1146 (acetal C—O).

TGA-MS Data

| Temperature/° C. | % Weight loss | Fragments observed on MS trace (m/z ratio) |
|---|---|---|
| 100 | 0.3 | 44 |
| 150 | 0.8 | 44 |
| 200 | 8.3 | 44, 55, 72, 101 |
| 250 | 23.1 | 44, 55, 72, 101 |
| 300 | 37.3 | 44, 55 |
| 350 | 44.9 | 44 |
| 400 | 49.3 | 44 |

Crosslinked Material 9 (m=1, n=3)

Monomer:Initiator ratio=57:1; Gel Content: 89% ($W_{initial}$, 0.144 g; $W_{final}$, 0.128 g); FT-IR before TGA (neat), $v/cm^{-1}$: 2939 (C—H), 1691 (C=O), 1135 (acetal C—O); FT-IR after TGA (neat), $v/cm^{-1}$: 2927 (C—H), 1693 (C=O), 1147 (acetal C—O).

TGA-MS Data

| Temperature/° C. | % Weight loss | Fragments observed on MS trace (m/z ratio) |
|---|---|---|
| 100 | 0.4 | 44 |
| 150 | 1.3 | 44 |
| 200 | 8.6 | 44, 55, 72, 101 |
| 250 | 21.4 | 44, 55, 72, 101 |
| 300 | 25.5 | 44, 55, 72, 101 |
| 350 | 30.6 | 44 |
| 400 | 34.4 | 44 |

While a number of embodiments of this invention have been represented, it is apparent that the basic construction can be altered to provide other embodiments that utilize the invention without departing from the spirit and scope of the invention. All such modifications and variations are intended to be included within the scope of the invention as defined in the appended claims rather than the specific embodiments that have been presented by way of example.

We claim:

1. A compound represented by the following structure:

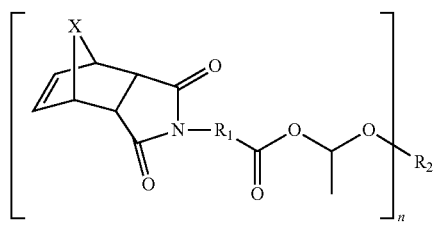

wherein X is independently $CH_2$ or O; $R_1$ is selected from the group consisting of unsubstituted or substituted alkyl, cycloalkyl, alkenyl, and aryl groups, wherein any of the before mentioned groups may be present with or without heteroatoms; $R_2$ is n-propyl and n is 1 to 3.

2. The compound according to claim 1, wherein X is $CH_2$; $R_1$ selected from the group consisting of $C_1$-$C_8$ alkyl and alkenyl groups, cyclopentane, cyclohexane, and cycloheptane groups, wherein any of the before mentioned groups may be present with or without heteroatoms; and n is 1 to 3.

3. A compound represented by the following structure:

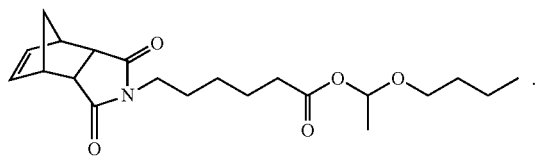 [SMILES: CCCCOC(C)OC(=O)CCCCCN1C(=O)C2C3C=CC(C3)C2C1=O]

4. A compound represented by the following general structure:

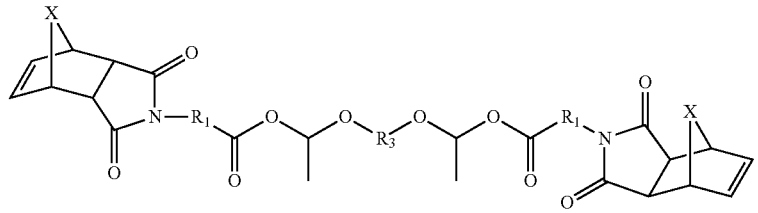

wherein X is independently $CH_2$ or O; $R_1$, and $R_3$ are independently selected from the group consisting of unsubstituted or substituted alkyl, cycloalkyl, alkenyl, and aryl groups, wherein any of the before mentioned groups may be present with or without heteroatoms; wherein each $R_1$ group is further independently selected from any of the before mentioned groups.

5. The compound according to claim 4, wherein X is $CH_2$; $R_1$ and $R_3$ are independently selected from the group consisting of $C_1$-$C_8$ alkyl and alkenyl groups, cyclopentane, cyclohexane, and cycloheptane groups, wherein any of the before mentioned groups may be present with or without heteroatoms.

6. The compound according to claim 5, wherein the compound is represented by the following structure:

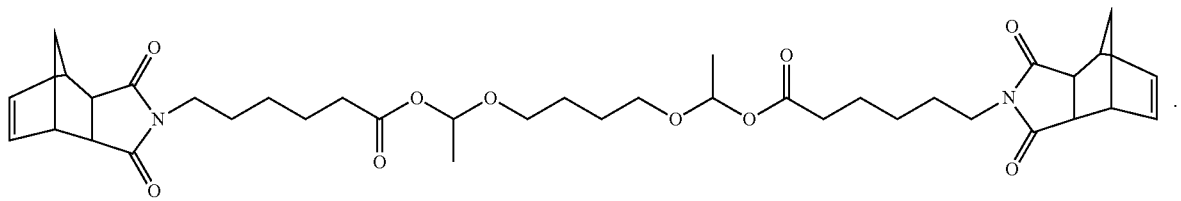 [SMILES: CC(OCCCCOC(C)OC(=O)CCCCCN1C(=O)C2C(C1=O)C1CC13C=CC23)OC(=O)CCCCCN1C(=O)C2C(C1=O)C1CC13C=CC23]

7. An adhesive, coating, encapsulation, personal care, oilfield, membrane, agricultural, or cleaning composition comprising a compound represented by the following structure:

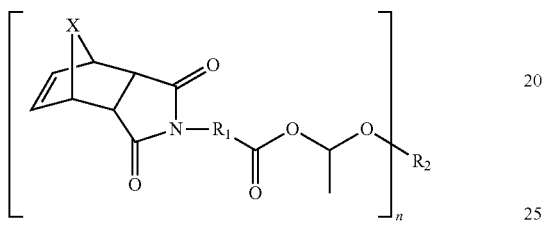

wherein X is independently $CH_2$ or O; $R_1$ is selected from the group consisting of unsubstituted or substituted alkyl, cycloalkyl, alkenyl, and aryl groups, wherein any of the before mentioned groups may be present with or without heteroatoms; $R_2$ is n-propyl, and n is 1 to 3.

8. An adhesive, coating, encapsulation, personal care, oilfield, membrane, agricultural, or cleaning composition comprising a compound represented by the following general structure:

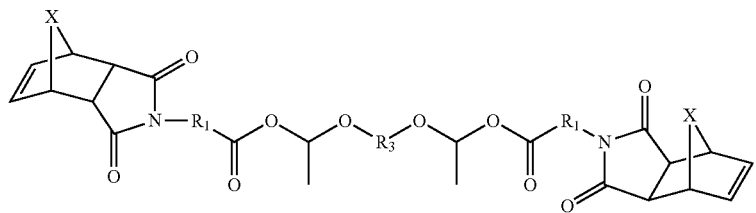

wherein X is independently $CH_2$ or O; $R_1$, and $R_3$ are independently selected from the group consisting of unsubstituted or substituted alkyl, cycloalkyl, alkenyl, and aryl groups, wherein any of the before mentioned groups may be present with or without heteroatoms; wherein each $R_1$ group is further independently selected from any of the before mentioned groups.

* * * * *